United States Patent [19]

Garland et al.

[11] Patent Number: 4,992,581

[45] Date of Patent: Feb. 12, 1991

[54] METHOD OF MANUFACTURING THROMBOXANE A$_2$ ANTAGONISTS

[75] Inventors: Robert B. Garland; Masateru Miyano, both of Northbrook, Ill.

[73] Assignee: National Research Development Corporation, London, England

[21] Appl. No.: 283,675

[22] Filed: Dec. 13, 1988

[51] Int. Cl.$^5$ ............................................. C07C 319/00
[52] U.S. Cl. ..................................... 562/427; 560/16; 562/401
[58] Field of Search ......................... 562/427; 514/562

[56] References Cited

U.S. PATENT DOCUMENTS

| | | | |
|---|---|---|---|
| 4,416,896 | 11/1983 | Nakane et al. | 549/463 X |
| 4,430,345 | 2/1984 | Jones et al. | 562/427 X |
| 4,438,136 | 3/1984 | Jones et al. | 562/426 X |
| 4,456,617 | 6/1984 | Nakane et al. | 549/463 X |
| 4,458,091 | 7/1984 | Jones et al. | 562/502 |
| 4,596,823 | 6/1986 | Jones et al. | 560/34 |

OTHER PUBLICATIONS

Hiemstra et al, *Tetrahedron Letters*, No. 25, pp. 2183–2186 (1977).
McMurry et al, *Tetrahedron Letters*, No. 24, pp. 979–982 (1983).
Lemiere et al., *J. Am. Chem. Society*, vol. 109, No. 5 (1987), pp. 1363–1370.
McMurry et al., *Tetrahedron Letters*, No. 21, pp. 4313–4316 (1980).
Plattner et al., *J. Am. Chem. Society*, vol. 93, No. 7, 1758–1761 (1971).
Wilson et al, Advances in Pros., Throm. & Leukotriene Res., vol. 14 (1985), pp. 393–425.
Nakane et al, Advances in Pros., Throm. & Leukotriene Res. (1985), vol. 15, p. 291.
Sprague et al, Advances in Pros, Throm. & Leukotriene Res. (1980), vol. 6, pp. 493–496.
Armstrong et al, *Br. J. Pharmac.* (1985) 84, pp. 595–607.

*Primary Examiner*—Werren B. Lone
*Assistant Examiner*—Vera C. Clarke
*Attorney, Agent, or Firm*—Nixon & Vanderhye

[57] ABSTRACT

This invention relates to several novel methods of manufacturing thromboxane A$_2$ inhibiting 7-[3-α-[1-[[(phenylamino)-thioxomethyl]hydrazono]ethyl]-bicyclo[2.2.1]-heptenoic acids.

4 Claims, No Drawings

NOVEL METHODS OF MANUFACTURING THROMBOXANE A₂ ANTAGONISTS

BACKGROUND OF THE INVENTION

The present invention provides novel compounds which are pharmacologically useful as thromboxane A₂ antagonist drugs. More specifically, the compounds of the present invention are orally active thromboxane A₂ antagonist agents which promote their effects through their ability to inhibit thromboxane A₂'s powerful induction of platelet aggregation and the platelet release reaction. It is thought that the thromboxane A₂ antagonists exhibit their activity by being able to occupy thromboxane receptor sites. In addition to its platelet aggregation action, thromboxane A₂ has been implicated in other potentially noxious actions on various body systems, including bronchoconstriction and pulmonary and systemic vasoconstriction. Thus thromboxane A₂ may be involved in the normal sealing of blood vessels following injury, but in addition may contribute to pathological intravascular clotting or thrombosis. Moreover, the constrictor actions of thromboxane A₂ on bronchiolar, pulmonary vascular and systemic vascular smooth muscle may be important in the development of several anaphylactic conditions, including bronchial asthma. There is also some evidence to implicate thromboxane A₂ in the pathogenesis of inflammation.

Thromboxane A₂ antagonists of the present invention belong to a group of bicycloheptenoic acids as partially exemplified in U.S. Pat. No. 4,596,823 to Jones, et al. The present invention also relates to novel pharmaceutical compositions comprising one or more of the active compounds of the invention in combination with suitable pharmaceutical carriers as well as methods of using such compounds and pharmaceutical compositions thereof in the treatment, prevention, or mitigation of disease states brought on by the activity of thromboxane A₂. In addition, the compounds can be used in in vitro diagnosis (e.g. in assays for thromboxane A₂ and the like). The invention further relates to novel methods of synthesis of the novel thromboxane A₂ antagonist compounds of the invention, as well as to novel intermediates used in the novel syntheses of the invention.

SUMMARY OF THE INVENTION

The present invention further provides intermediate compounds of the general formula II:

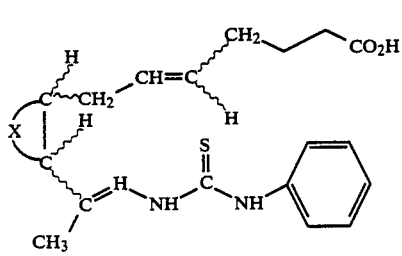
(I)

and the pharmaceutically acceptable salts thereof, wherein X is a bicyclic ring of the structure and orientation

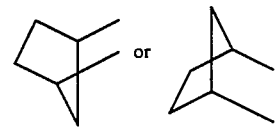

with the proviso that racemic modifications are not included herein.

The present invention further provides intermediate compounds of the general formula II:

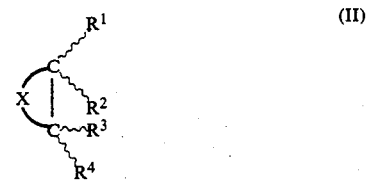
(II)

wherein X is a bicyclic ring of the structure

(II a.)

or

(II b.)

R¹ is hydrogen;
R² is of the formula

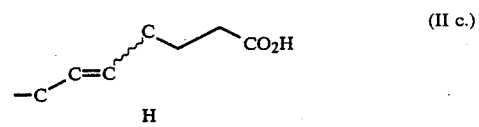
(II c.)

R³ is hydrogen and
R⁴ is

wherein R⁵ is alkyl of from one to ten carbon atoms or

wherein R⁵ is as defined above.

The present invention further provides intermediate compounds of the general formula III:

wherein [X. is a heterocyclic ring of a structure selected from the group consisting of

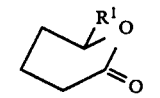 (III a.)

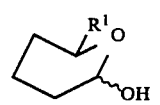 (III b.)

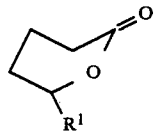 (III c.)

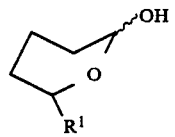 (III d.)

wherein $R^1$ is alkyl of from one to ten carbon atoms.

The present invention further provides intermediate compounds of the general formula IV:

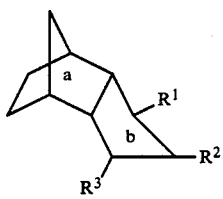 (IV)

wherein $R^1$, $R^2$, or $R^3$ are independently hydrogen, alkyl of from one to ten carbon atoms or a keto group, with the proviso that only one keto group may be present on the 'b' ring.

The present invention further provides intermediate compounds of the general formula V:

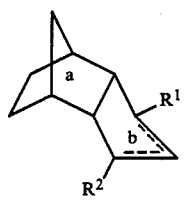 (V)

wherein $R^1$ and $R^2$ are independently hydrogen, alkyl of from one to ten carbon atoms or trifluoro sulfonimide; and which can be saturated or unsaturated in the 'b' ring, with the proviso that there can be no more than one degree of unsaturation in the 'b' ring.

The present invention further provides intermediate compounds of the general formula VI:

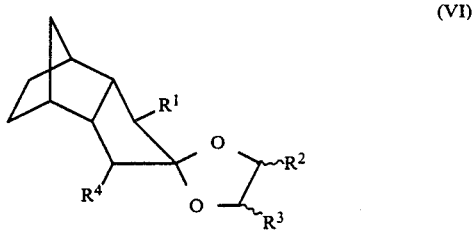 (VI)

wherein $R^1$, $R^2$, $R^3$ and $R^4$ are independently hydrogen or alkyl of from one to ten carbon atoms.

The present invention furthermore relates to a process for selected enantiomers of the compound of the general formula VII:

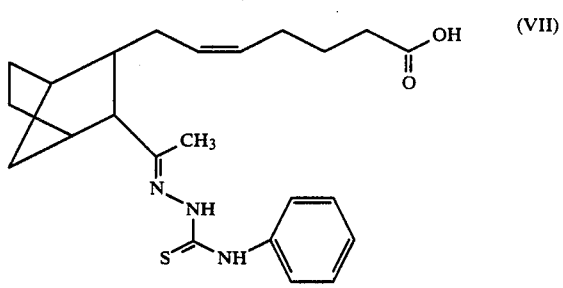 (VII)

comprising the step of resolving a compound of the general formula

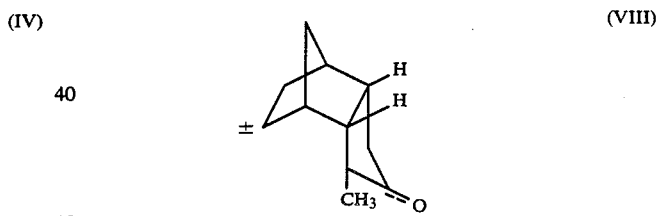 (VIII)

into the respective enantiomers of the formulas

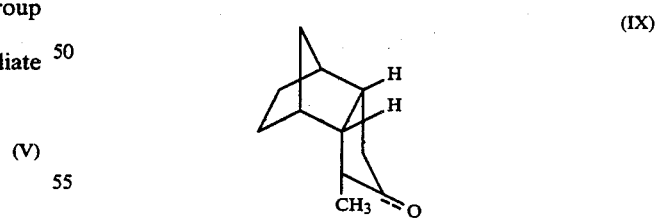 (IX)

and

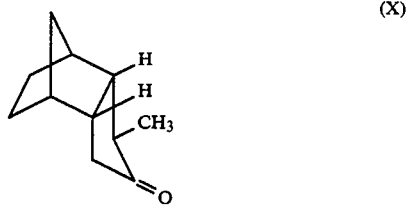 (X)

by reacting the compound of formula II with a diol whose hydroxyl functions are attached to adjacent carbon atoms.

This diol is preferably one whose hydroxyl functions are attached to adjacent carbon atoms, is more preferably one in which the adjacent chiral carbon atoms have symmetry elements that define $C_2$ symmetry, and most preferably the diols are selected from the group consisting of (2R,3R)-2,3-butanediol or (2S,3S)-2-3-butanediol.

More specifically, this particular process of the invention proceeds by (a) reacting a compound of the general formula

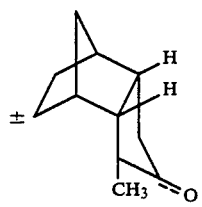

(XI)

with a compound selected from the group consisting of (2R,3R)-2,3-butanediol or (2S,3S)-2,3-butanediol;

(b) hydrolyzing the product of (a);

(c) oxidizing the product of (b) by peracid oxidation;

(d) reducing the product of (c); and (e) oxidizing the product of (d) to a ketone which is isomerized with base to the stable isomer.

A second process of the present invention is provided herein for making a compound of the formula

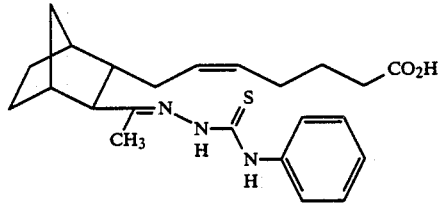

(XII)

comprising the steps of (a) reacting a compound of the formula

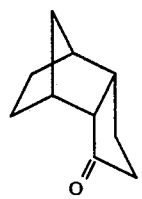

(XIII)

with a triflating reagent, that is, a trifluoromethylsulfonating reagent, in the presence of a base to form a compound of the formula

(XIV)

which is then alkylated to form a product of the formula

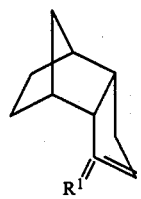

(XV)

wherein $R^1$ is alkyl of from 1 to 10 carbon atoms in length.

More specifically, this second process of the invention proceeds by (a) hydrogenating a compound of the formula

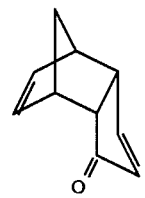

(XVI)

(b) converting the product of (a) to its enol triflate;
(c) reacting the product of (b) with lithium dimethyl cuprate
(d) hydroborating the product of (c) and oxidizing to a ketone; and
(e) isomerizing the product of (d).

A third method is provided for by the present invention for making compounds of the general formula

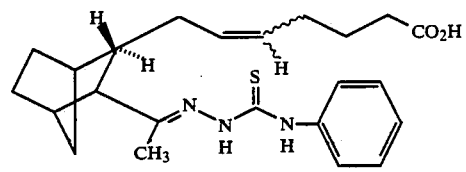

(XVII)

which can be either the cis or the trans double bond eometric isomer, comprising the steps of (a) reacting a compound of the formula

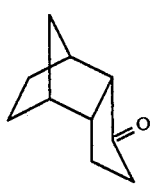

(XVIII)

with a triflating reagent, in the presence of a base to form a compound of the formula

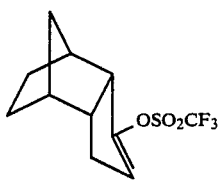

(XIX)

which is then alkylated to form a compound of the formula

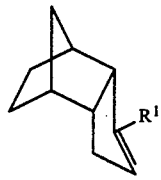

(XX)

wherein $R^1$ is alkyl of from 1 to 10 carbon atoms in length.

More specifically, this method proceeds by the steps of (a) reacting a compound of the formula

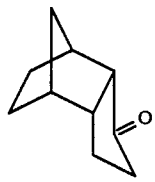

(XVIII)

in the presence of a base to form a anion of the formula

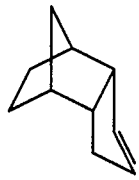

(XIX)

which is then alkylated to form a compound of the formula

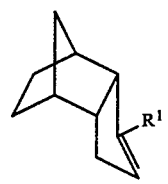

(XX)

wherein $R^1$ is alkyl of from 1 to 10 carbon atoms in length;
(b) hydroborating and oxidizing the product of (a)
(c) oxidizing the product of (b) by peracid oxidation;
(d) reducing the product of (c);
(e) reacting the product of (d) with (4-carboxybutyl)-tri-phenylphosphonium bromide; and (f) reacting the product of (e) with 4-phenyl-3-thiosemicarbazide.

The compounds of the pharmaceutical compositions encompassed above are useful in the thromboxane $A_2$ antagonist methods of the invention.

DETAILED DESCRIPTION OF THE INVENTION

As used herein, the following expressions have the following definitions and meanings.

"Alkyl" is defined to include straight or branched carbon-carbon linkages having the number of carbon atoms indicated, preferably 1 to 10. Representative alkyl moieties of any of the substituent groups include methyl, ethyl, propyl, butyl, pentyl, hexyl, heptyl, octyl, nonyl and decyl, and the corresponding other isomeric forms thereof. Any of the alkyl moieties mentioned may have one or more degrees of unsaturation present to become an alkenyl moiety. Again, other corresponding isomeric forms are included, such as geometric isomers, diastereoisomers and enantiomers.

"$C_2$ symmetry" means that a molecule possesses a simple twofold axis as illustrated:

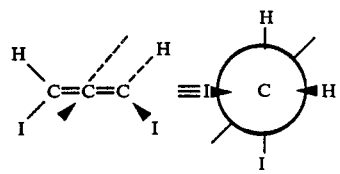

See W. J. LeNoble, *Highlights of Organic Chemistry*, pp. 161,162, Marcel Dekker (1974).

"Pharmaceutically acceptable non-toxic salts" means that to the extent that the compounds herein may also be prepared as addition salt forms thereof, that such forms are included in the present compound formulas. Typical of such "pharmaceutically acceptable salts" are those non-toxic pharmaceutically acceptable salts such as salts in which the cationic portion is taken from the alkali metals, especially sodium and potassium, from the alkaline earth metals, especially calcium, and the ammonium cation.

"Pharmacologically effective amount" shall mean a dosage or dosage regimen utilizing the compounds of the present invention that have been selected in accordance with a variety of factors including the type, species, age, weight, sex and medical condition of the patient; with the severity of the condition to be ameliorated; the route of administration; the renal and hepatic function of the patient; the route of administration; and the particular compound employed or mixtures thereof. An ordinarily skilled veterinarian or physician can readily determine and prescribe the effective amount of the drug required to prevent, treat or arrest the progress of the condition.

Dosages of the compounds of the present invention, when used for the indicated effects, will range between about 0.0l/mg/kg to 100 mg/kg and preferably 0.1 mg/kg to 10 mg/kg. Advantageously, the compounds of the present invention may be administered in a single daily dose or the total daily dosage may be administered in equal divided dosages of two, three or four times daily.

The compounds of the present invention can be administered in such oral dosage forms as tablets, capsules, pills, powders, granules, elixirs, tinctures, suspensions, syrups, emulsions, shake solutions, colloids or suspensions. Likewise, they may also be administered in intravenous, intraperitoneal, subcutaneous or intramuscular form, all using forms known to those of ordinary skill in the pharmaceutical arts. In general, the preferred form of administration is oral.

In the pharmaceutical compositions and methods of the present invention, the foregoing compounds described in detail above will form the active ingredients and will typically be administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional and pharmaceutical practices.

For instance, for oral administration in the form of tablets or capsules, the active drug components may be combined with an oral non toxic pharmaceutically acceptable inert carrier such as lactose, starch, sucrose, glucose, methylcellulose, magnesium stearate, dicalciumphosphate, calciumsulfate, mannitol, sorbitol and the like; for oral administration in liquid form, the active drug components may be combined with any oral non toxic pharmaceutically acceptable inert carrier such as ethanol, glycerol, water, and the like. Moreover, when desired or necessary, suitable binders, lubricants, disintegrating agents and coloring agents can also be incorporated in the mixture. Suitable binders include starch, gelatin, natural sugars such as glucose or β-lactose, corn sweeteners, natural and synthetic gum such as acacia, tragacanth or sodium alginate, carboxymethylcellulose, polyethylene glycol and waxes. Lubricants for use in these dosage forms include boric acid, sodium benzoate, sodium acetate, sodium chloride and the like. Disintegrators include, without limitation, starch, methylcellulose, agar, bentonite, xanthan gum and the like.

Primarily representative of the more preferred compounds in accordance with the present invention are those wherein the compound has the general formula I:

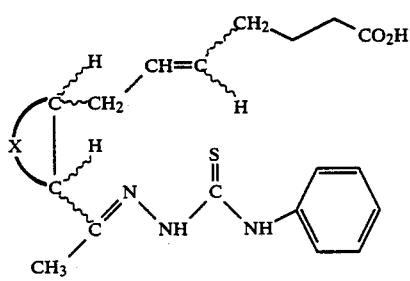

and the pharmaceutically acceptable salts thereof, wherein X is a bicyclic ring of the structure:

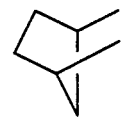

or

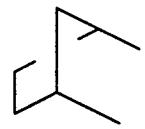

The especially preferred embodiments of this invention include those compounds as described above, and which are: 7-[3α-[1-[[(Phenylamino)thioxomethyl]hydrazono]ethyl]-1R, 1α,4α-bicyclo-[2.2.1]hept-2β-yl]-5Z-heptenoic acid:

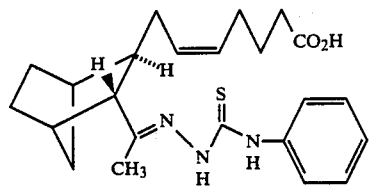

7-[3α-[1-[[(Phenylamino)thioxomethyl]hydrazono]ethyl]1S, 1α,4α-bicyclo [2.2.1]hept 2β-yl]5Z heptenoic acid:

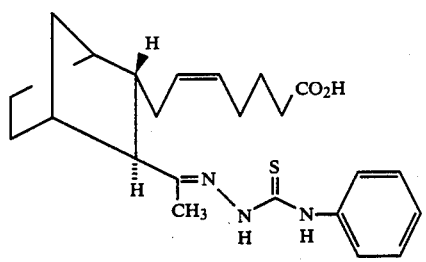

and 7-[3α-[1-[[(Phenylamino)thioxomethyl]hydrazono]ethyl]- 1R,1α,4α-bicyclo-[2.2.1]hept-2β-yl]-5E-heptenoic acid:

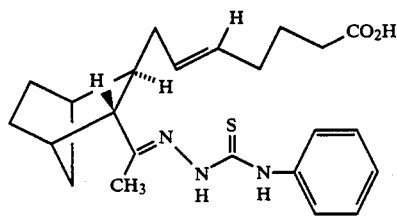

Representative of intermediate compounds of the present invention are those of the general formula II:

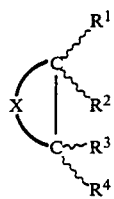

wherein X is a bicyclic ring of the structure

or

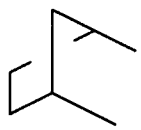

$R^1$ is hydrogen;
$R^2$ is of the formula

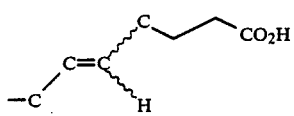

$R^3$ is hydrogen and
$R^4$ is

wherein $R^5$ is alkyl of from one to ten carbon atoms or

wherein $R^5$ is as defined above.

Most especially preferred intermediate compounds that fall within the structure of general formula II are:
7-(3α-Acetyl-1R,1α,4α-bicyclo[2.2.1]hept-2β-yl-5Z-heptenoic acid:

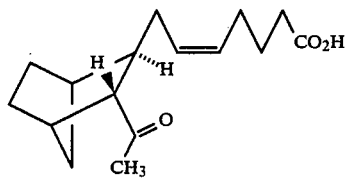

7-(3α-(Acetyl-1S,1α,4α-bicyclo[2.2.1]hept-2β-yl)-5Z-heptenoic acid:

(II)

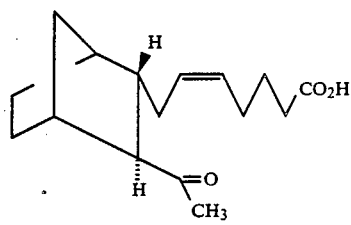

7-(3α-(Acetyl-1R,1α,4α-bicyclo[2.2.1]hept-2β-yl)-5E-heptenoic acid:

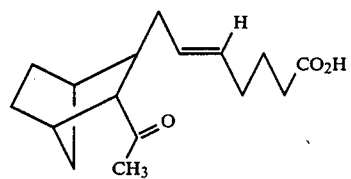

7-(3α-(Acetyl-1R,1α,4α-bicyclo[2.2.1]hept-2β-yl)-5Z-heptonic acid:

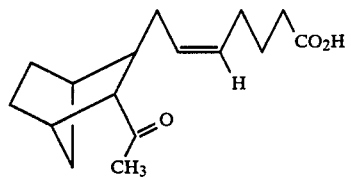

7-[3β-1S*-Hydroxyethyl-1R,1α,4α-bicyclo[2.2.1]hept-2β-yl)-5E-heptenoic acid:

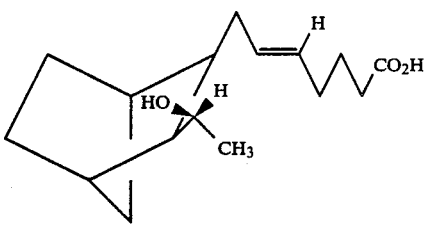

7-[3β-1S*-Hydroxyethyl-1R,1α,4α-bicyclo[2.2.1]hept-2β-yl)-5Z-heptenoic acid:

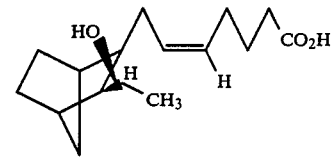

7-[3α-(Acetyl-1S,1α,4α-bicyclo[2.2.1]hept-2β-yl)-5Z-heptonic acid:

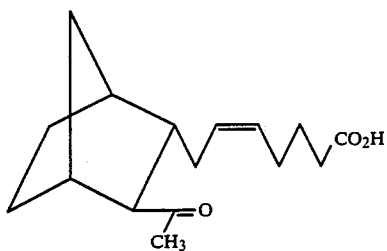

7-[3α-(Acetyl-1S,1α,4α-bicyclo[2.2.1]hept-2β-yl)-5E-heptenoate:

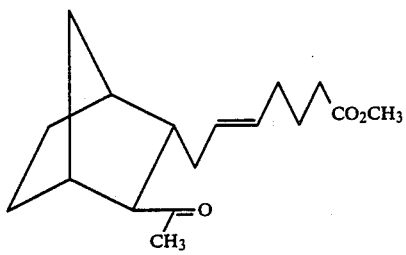

and Methyl 7-(3α-Acetyl-1S,1α,4α-bicyclo[2.2.1]hept-2β-yl)-5Z-heptenoate:

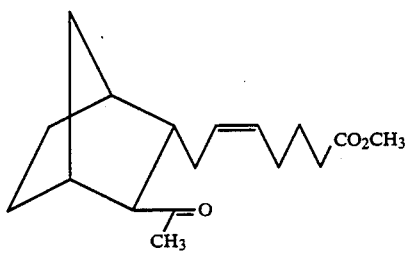

Secondarily representative of intermediate compounds of the claimed invention are those of the general formula III:

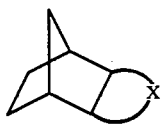 (III)

wherein X is a heterocyclic ring of a structure selected from the group consisting of

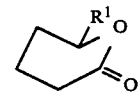

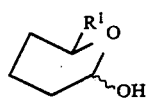

-continued wherein $R^1$ is alkyl of from one to ten carbon atoms.

Most especially preferred compounds that fall within the structure of general formula III are: 4aα,8aα-Octahydro-1R,1α-methyl-5α,8α-methano-1H-2-benzopyran-3-ol:

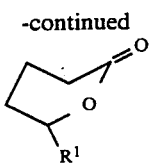

4aα,8aα-Octahydro-1S,1α-methyl-5α,8α-methano-1H-2-benzopyran-3-ol:

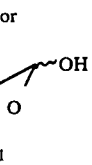

4aα,8aα-Octahydro-1R,1α-methyl-5α,8α-methano-3H-2-benzopyran-3-one:

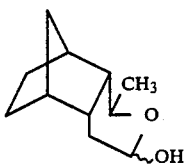

4aα,8aα-Octahydro-1S,1α-methyl-5α,8α-methano-3H-2-benzopyran-3-one:

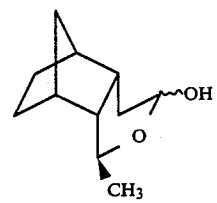

4aβ,8aβ-Octahydro-1R,1α-methyl-5β,8β-methano-1H-2-benzopyran-3-ol:

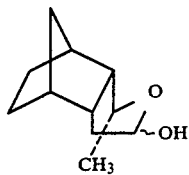

4aβ,8aβ-Octahydro-1R,1α-methyl-5β,8β-methano-3H-2-benzopyran-3-one:

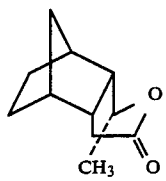

4aα,8aα-Octahydro-1S,1α-methyl-5α,8α-methano-1H-2-benzopyran-3-ol:

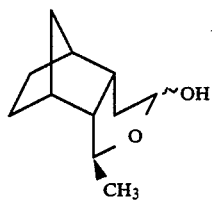

and 4aα,8aα-Octahydro-1S,1α-methyl-5α,8α-methano-3H-2-benzopyran-3-one:

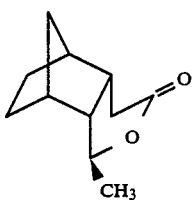

Thirdly representative of the intermediate compounds of the present invention are those of the general formula IV:

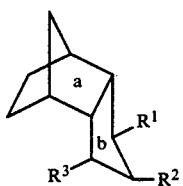

(IV)

wherein $R^1$, $R^2$, or $R^3$ are independently hydrogen, alkyl of from one to ten carbon atoms or a keto group, with the proviso that only one keto group may be present on the 'b' ring.

Especially preferred compounds found within the general formula of IV are: 3aR,3aα,7aα-Octahydro-4α,7α-methano-1H-inden-1-one:

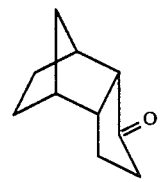

3aα,7aα-Octahydro-1R,1α-methyl-4α,7α-methano-2H-inden-2one:

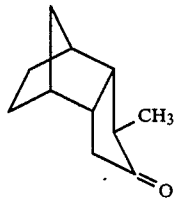

3aβ,7aβ-Octahydro-1R,1α-methyl-4β,7β-methano-2H-inden-2-one:

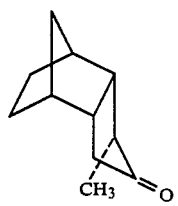

3aβ,7aβ-Octahydro-1S,1α-methyl-4β,7β-methano-2H-inden-2-one:

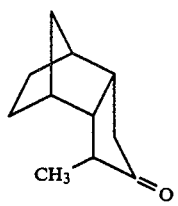

3aα,7aα-Octahydro-1S,1α-methyl-4α,7α-methano-2H-inden-2-one:

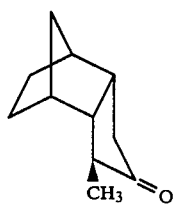

and 3aS,3aα,7aα-Octahydro-4α,7α-methano-1H-inden-1-one:

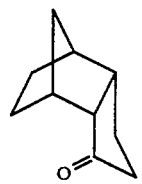

Fourthly representative of intermediate compounds of the present invention are those of the general formula V:

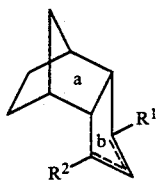

(V)

wherein R¹ and R² are independently hydrogen, alkyl of from one to ten carbon atoms or trifluoromethylsulfonyloxy; and which can be saturated or unsaturated in the 'b' ring, with the proviso that there can be no more than one degree of unsaturation in the 'b' ring.

Especially preferred compounds found within the general formula of V are: 3aS,3aα,4,5,6,7,7a-Hexahydro-4α,7α-methano-1H-indene:

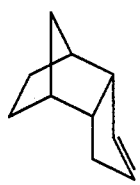

3aR,3aα,4,5,6,7,7a-Hexahydro-4α,7α-methano-1H-indene:

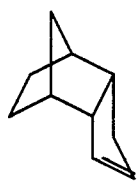

3aS,3aα,4,5,6,7,7aα-Hexahydro-3-methyl-4α,7α-methano-1H-indene:

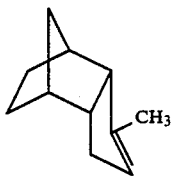

3aR,3aα,4,5,6,7,7aα-Hexahydro-3-methyl-4α,7α-methano-1H-indene:

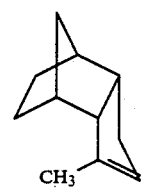

3aS,3aα,4,5,6,7,7aα-Hexahydro-4α,7α-methano-1H-inden-3-yl trifluoromethanesulfonate:

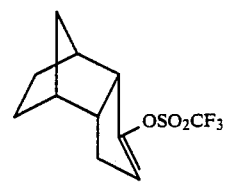

3aR,3aα,4,5,6,7,7aα-Hexahydro-4α,7α-methano-1H-inden-3-yl trifluoromethanesulfonate:

3aβ,7aβ-Octahydro-1R,1α-methyl-2β-hydroxy-4β,7β-methano-2H-indene:

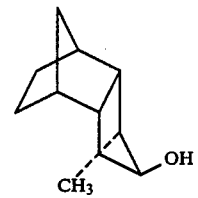

3aβ,7aβ-Octahydro-1S,1α-methyl-2β-hydroxy-4β,7β-methano-2H-indene:

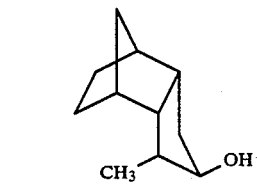

Fifthly representative of intermediate compounds of the present invention are those of the general formula VI:

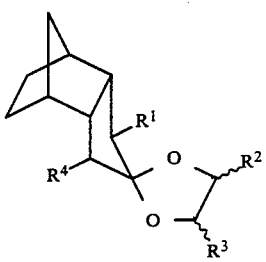

(VI)

wherein $R^1$, $R^2$, $R^3$ and $R^4$ are independently hydrogen or alkyl of from one to ten carbon atoms.

Especially preferred compounds found within the general formula of VI are:

3'aα,7'aα-Octahydro-1'R,1'α,4S*,5S*-trimethyl-spiro[1,3-dioxolane-2,2 -[4'α,7'α]methano-[2H]indene]:

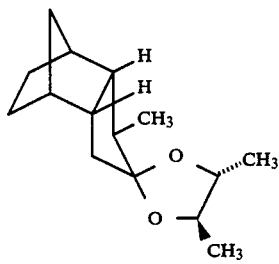

3'aα,7'aα-Octahydro-1'R,1'α,4R*,5R*-trimethyl-spiro[1,3-dioxolane-2,2'-[4'α,7'α]methano[2H]indene:

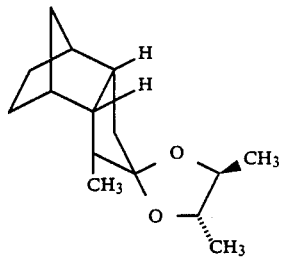

3'aα,7'aα-Octahydro-1'S,1'α,4R*,5R*-trimethyl-spiro[1,3-dioxolane-2,2'-[4'α,7'α]methano-[2H]indene:

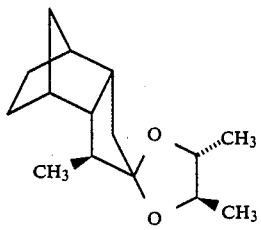

3'aα,7'aα-Octahydro-1'S,1'α,4S*,5S*-trimethyl-spiro[1,3-dioxolane-2,2'-[4'α,7'α]methano[2H]indene]:

The compounds of the invention can be prepared by methods which are in themselves known, under reaction conditions which are known as suitable for the reactions mentioned. In these reactions, it is also possible to make use of variants which are in themselves known, but are not mentioned here in greater detail. The compounds of the invention are readily prepared according to one of the following reaction schemes or modifications thereof using readily available starting materials, reagents and conventional synthesis procedures.

Scheme I

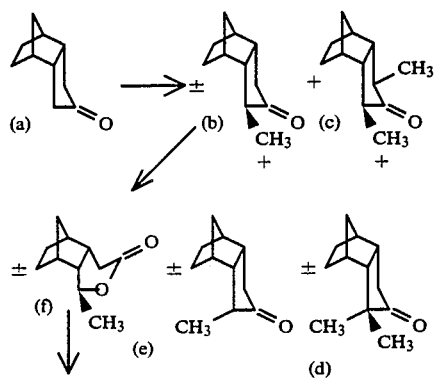

4,992,581
-continued
Scheme I
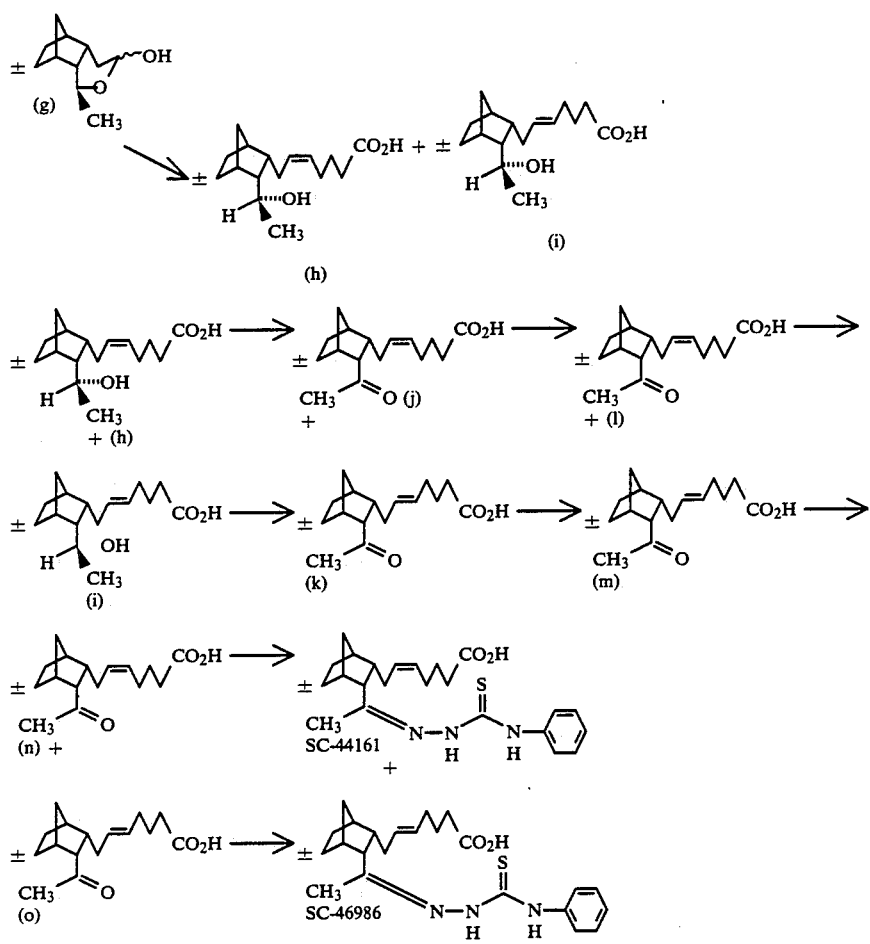
Scheme II
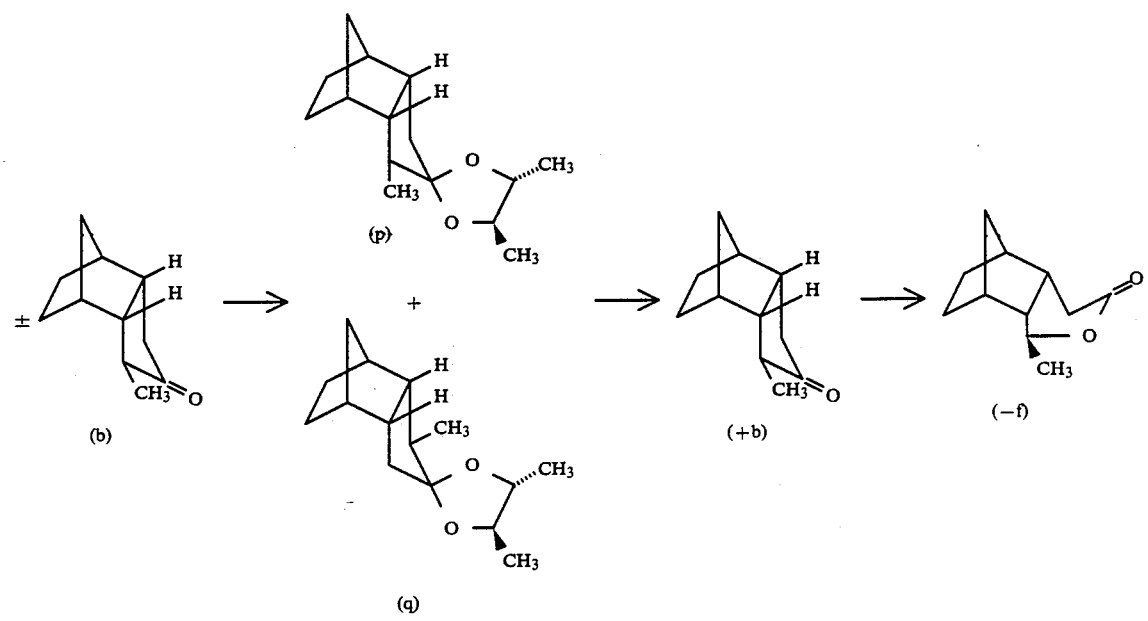

-continued
Scheme II
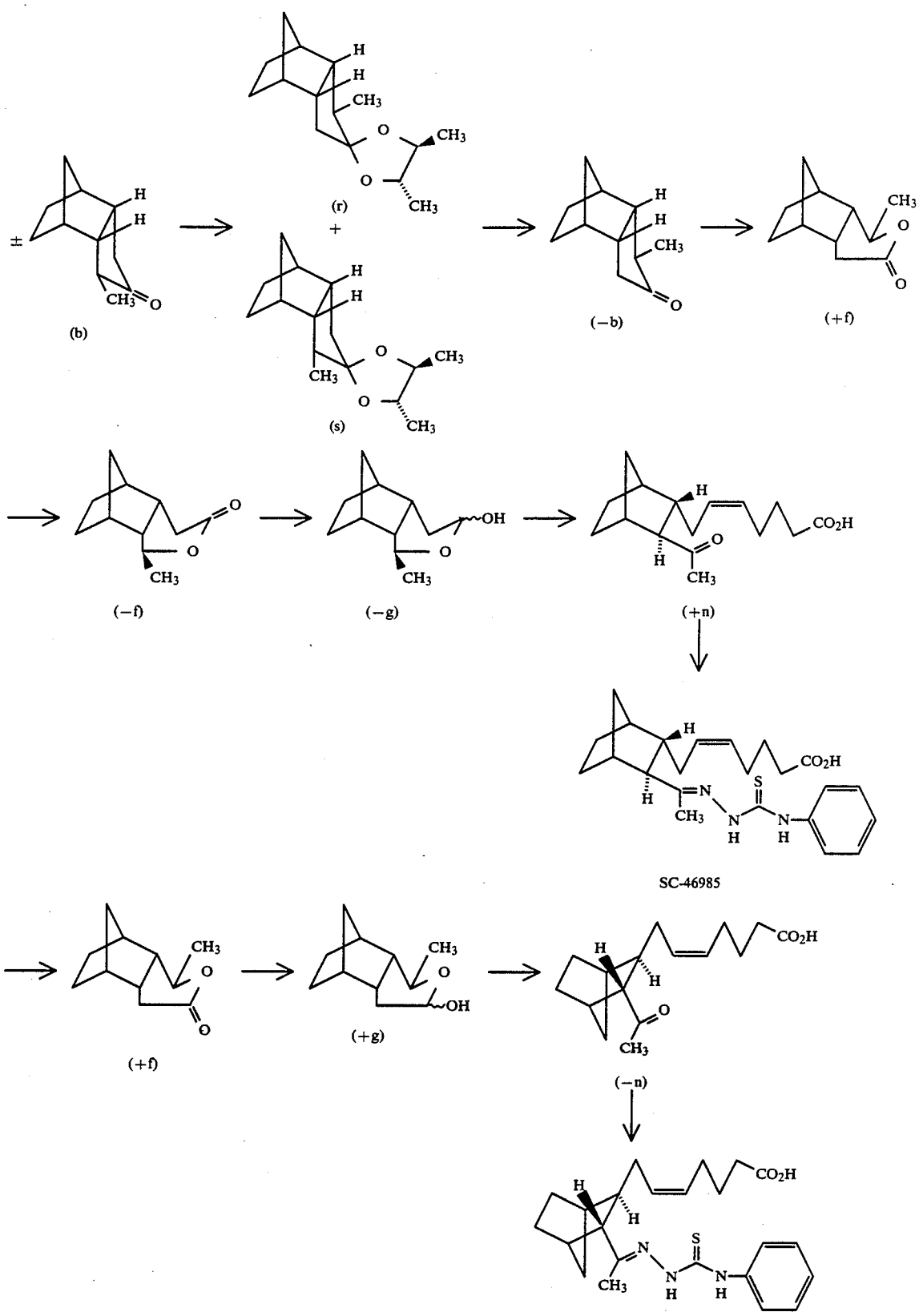

Scheme III
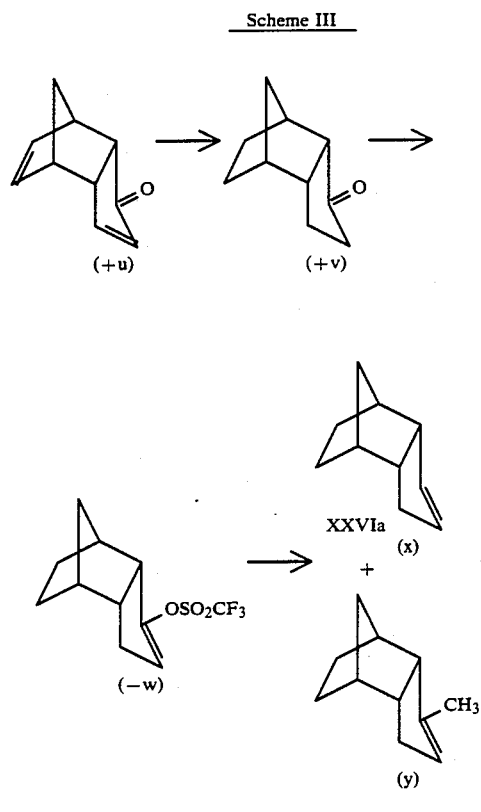
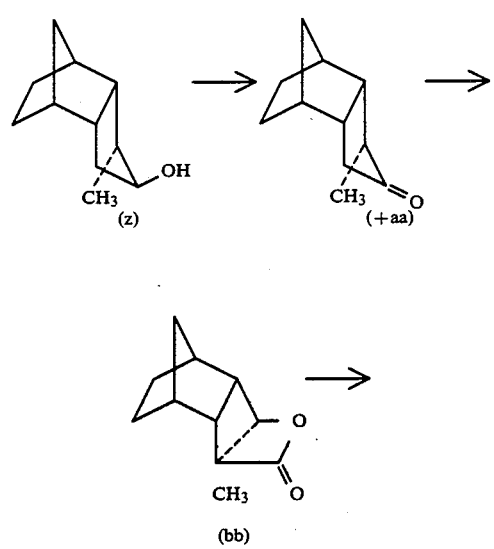
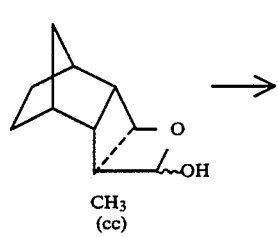
-continued
Scheme III
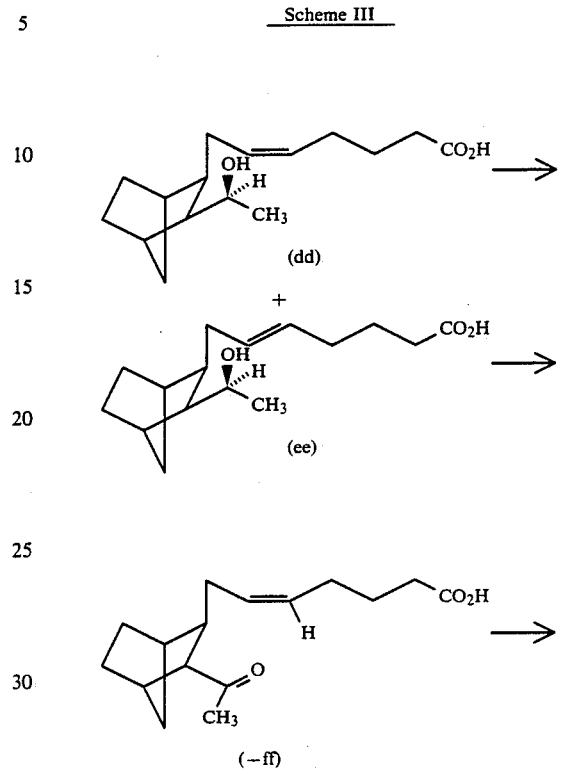
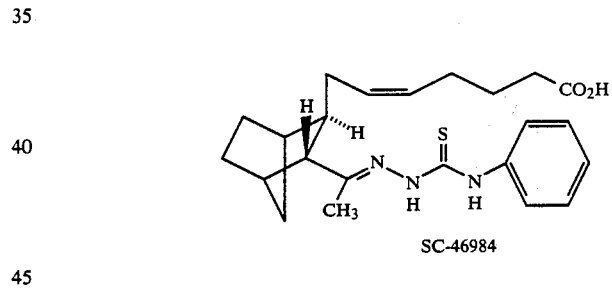
SC-46984
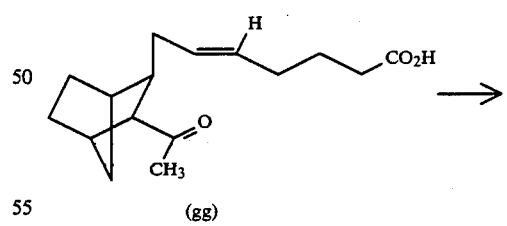
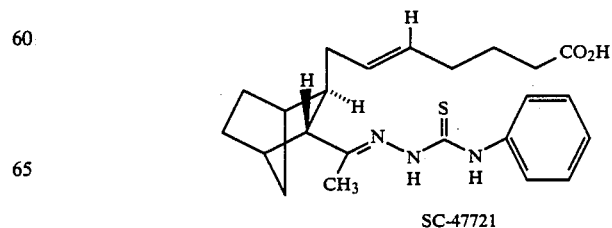
SC-47721

Scheme IV

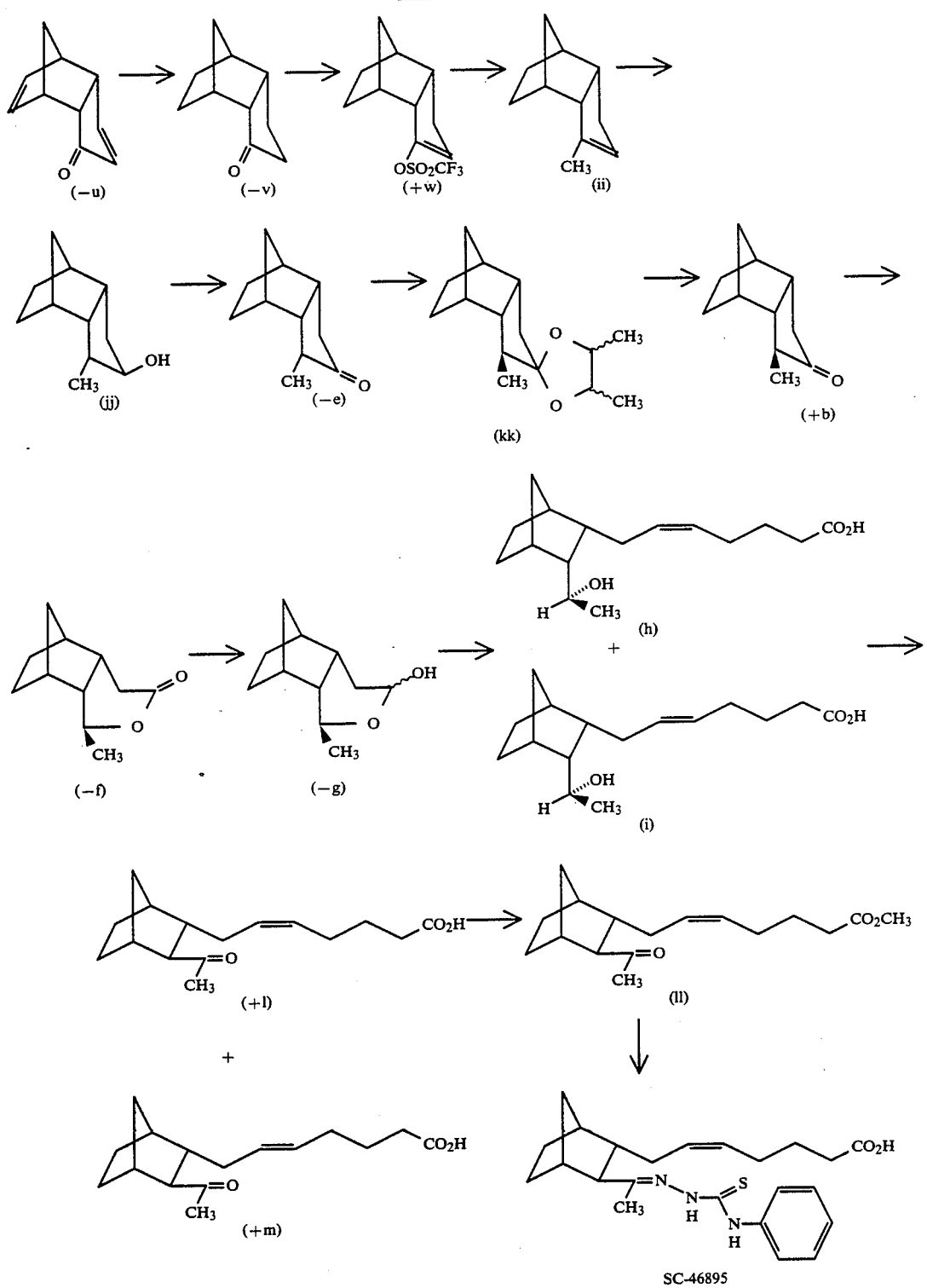

SC-46895

The following examples will further illustrate details of the various methods of the various compounds of the invention. The invention, which is set forth in the foregoing disclosure, is not to be construed as limited in spirit or in scope by these examples. Those skilled in the art will readily understand that known variations of the conditions of the following preparative procedures can be used to prepare these compounds. All temperatures are degrees Celsius unless otherwise noted. In these reactions, it is also possible to make use of variations which are in themselves known, but are not mentioned here in greater detail.

SYNTHESIS OF SC 44161

EXAMPLE 1

(±)3aα,7aα-Octahydro-1α-methyl-4α,7α-methano-2H-inden-2-one, (b). To a solution of 6.9 mL (5.93 g, 41.9 mmole) of N-isopropylcyclohexyl-amine in 20 ml of dry THF cooled in a -78° bath was added 25 mL of 1.58 m n-butyllithium in hexane. After 15 min a solution of 5.62 g (37.5 mmole) of (a) in 20 mL of THF was added over 20 min. This mixture was stirred 15 min and 5 mL (11.4 g, 80 mmole) of methyl iodide was added. After 30 min more, the mixture was allowed to warm to room temperature and 50 mL water was added. The mixture was extracted twice with ether, washed with water and brine and then dried over sodium sulfate. The solvents were evaporated and the residue was chromatographed (Flash, hexane-EtOAc 99:1) to provide first 596 mg (9%) of 3aα,7aα-octahydro-1α, 3α-dimethyl-4α,7α-methano-2H-inden-2-one, (c), followed by 3.81 g (62%) of (b), and then a small amount of crude (a). In some runs the early part of the (b) fraction contained (±)3aα,7aα-octahydro-1,1-dimethyl-4α,7α-methano-2H-inden-2-one, (d). In a run which was allowed to stand at room temperature overnight before workup, a small amount of the isomeric (±)3aβ-octahydro-1α-methyl-4β,7β-methano-2H-inden-2-one, (e), followed the main product closely. This isomer also forms under acidic equilibration.

EXAMPLE 2

(±)4aα,8aα-Octahydro-1α-methyl-5α,8α-methano-3H-2-benzopyran-3-one, (f). To a solution of 3.81 g (23.2 mmole) of (b) in 50 mL of dry methylene chloride was added 5.5 g (4.67 g, 27 mmole) of 85% m-chloroperoxybenzoic acid. After three days the solids were removed by filtration and rinsed with hexane. The filtrate was washed with sodium bicarbonate, water and brine. After evaporation of solvents chromatography (Flash, hexane-EtOAc 98:2) provided 47 mg crude (b) with aryl containing byproduct. This was followed by 4.02 g (96%) of (f). Crystallization from a small amount of hexane provided a solid melting at 51°-52.5°.

EXAMPLE 3

(±)4aα,8aα-Octahydro-1α-methyl-5α,8α-methano-1H-2-benzopyran-3-ol, (g). A solution of 4.02 g (22.3 mmole) of (f) in 5 mL of toluene was chilled in a -78° bath and 30 mL of 1 M DIBAL in toluene was added and stirred at −78° for 2 h. The mixture was quenched cautiously with 5 mL of MeOH After warming to room temperature, 50 mL more MeOH was added. The solid was removed by filtration, rinsing thoroughly with MeOH. The filtrate was evaporated, and the residue was crystallized from hexane to provide 3.23 g of (g), mp 93°-94°. Chromatography of the mother liquors (Flash, hexane-EtOAc 4:1-1:1) provided a small amount of crude (f) followed by a product fraction which was crystallized from hexane to provide an additional 0.33 g of (g). Total yield: 3.56 g (88%).

EXAMPLE 4

(±)7-[3β-(1S-Hydroxyethyl)-1α,4α-bicyclo[2.2.1]hept-2β-yl]-5Z-heptenoic acid, (h). To a suspension of 13.5 g (30.6 mmole) freshly crushed and dried (60°, high vac) (4-carboxybutyl)triphenylphosphonium bromide in 75 mL dry THF was added 60 mL of 1 M sodium (bistrimethylsilyl)amide in THF. The mixture was stirred at room temperature for 18 h under nitrogen and then a solution of 3.38 g (18.5 mmole) of (g) in 50 mL of THF was added over 10 min. The temperature rose from 27° to 35° during the addition. During 1 h the color faded quickly and more white solids formed. After the addition of 100 mL of water the mixture was extracted with ether. The aqueous layer was acidified with 10% HCl and extracted twice with ether washing with water and brine. After being dried over sodium sulfate the solvents were evaporated and the residue was chromatographed on a short CC-4 column (hexane-EtOAc, 4:1) to provide 4.90 g (99%) of a crude product fraction consisting of about 90% (h) and 10% of the 5E isomer, (i). Traces of (g) could be recovered from the first ether extraction.

EXAMPLE 5

(±)7-(3β-Acetyl 1α,4α-bicyclo[2.2.1]hept-2β-yl)-5Z-heptenoic acid, (j) and (±)7-(3α-acetyl-1α,4α-bicyclo[2.2.1]hept-2β-yl)-5Z-heptenoic acid, (1). A solution of 4.90 g (18.4 mmole) of crude (h) in 150 mL of acetone was chilled in an ice bath and titrated with Jones reagent (5.5 mL). The supernatant was decanted and concentrated to ca. 20 mL which was recombined with the solids and 100 mL of water. The mixture was extracted with ether. After washing with water and brine followed by drying over sodium sulfate the solvents were evaporated to leave 4.60 g of crude (j) with 10% of the 5E isomer, (k) which had partially isomerized to (1) and its 5E isomer (m). This material was dissolved in 50 mL of 1 N NaOH and stirred at room temperature for 1 h. After acidification with 10% HCl the product was extracted with ether which was washed with water and brine and dried over sodium sulfate. After evaporating solvents chromatography on a short CC-4 column (hexane-EtOAc 4:1) provided 4.38 g (90%) of a mixture containing ca. 90% (1) and 10% (m). No trace of (j) or (k) could be detected.

EXAMPLE 6

(±)7-[3α[[(Phenylamino)thioxomethyl]hydrazono]ethyl]1α,4α-bicyclo[2.2.1]hept-2β-yl]-5Z-heptenoic acid, (SC-44161). A solution of 1.20 g (4.5 mmole) of the mixture of (1) and (m) and 0.85 g (5.08 mmole) of 4-phenyl-3-thiosemicarbazide in 5 mL of pyridine was stirred at room temperature for 22 h. A solution of the mixture in 100 mL of methylene chloride was washed twice in 100 mL 5% HCl, water and brine. After drying over sodium sulfate and evaporation of solvent the residue was crystallized from 10 mL of ether to provide 1.364 g (73%) of SC-44161, mp 129°-132°. If necessary SC-44161 can be recrystallized by solution in methylene chloride, filtration, evaporation to a small volume and addition of ether.

SYNTHESIS OF SC-46984 and SC-46985

EXAMPLE 7

A solution of 2.26 g (13.8 mmole) of (b), 1.07 g (11.9 mmole) of (2R-,3R)-2,3-butanediol and 10 mg of camphorsulfonic acid in 40 mL of benzene was refluxed under a Dean-Starke trap for 12 h and then distilled to a volume of ca. 10 mL. After the addition of a few drops of Et₃N and concentration in vacuo, the residue was chromatographed (Flash, hexane—hexane-EtOAc 49:1) to provide 1.95 g of a product fraction followed by 430 mg of (b) enriched in the 1-enantiomer and then by 66 mg of (e) enriched in the d-enantiomer. The product fraction was repeatedly chromatographed (LPLC Woelm, hexane-Et₂O 49:1) cutting small fractions arbitrarily and combining those with >90% diastereomeric purity. The major isomer was 3'aα,7'aα-octahydro-1's,1'α,4S*-5S*-trimethyl-spiro[1,3-dioxolane-2,2'-[4'α,7'α]methano[2H]indene], (p), which was also the faster moving eventually provided 851 mg (92% (p) and 8% 3'aα,7'aα-octahydro-1'R,1'α,4R*,5R*-trimethyl-spiro[1,3-dioxolane-2,2'-[4'α,7'α]methano[2H]indene, (g), based on ¹³C NMR). The 430 mg of recovered (b), 300 mg of (2S,3S)-2,3-butanediol and 5 mg of camphorsulfonic acid in 35 mL of benzene was refluxed under a Dean-Starke trap for 16 h. After cooling, adding Et₃N and evaporating in vacuo, Flash Chromatography as above provided 636 mg of product fraction followed by a mixture of 48 mg of (b) and (e) isomers. LPLC of the product fractions as above provided 271 mg of the faster moving fractions consisting of 95% 3'aα,7'aα-octahydro-1'R,1'α,4S*,5S*-trimethyl-spiro[1,3-dioxolane-2,2'-[4'α,7'α]methano-[2H]indene], (r), and 5% 3'aα,7'aα-octahydro-1'S,1'α,4R*,5R*-trimethyl-spiro[1,3-dioxolane-2,2'-[4'α,7'α]methano[2H]indene, (p). The NMR analysis was based on the relative peak heights for a methylene carbon at ca. 35.4 ppm in isomers (p) and (r) vs. 34.7 ppm in isomers (g) and (s), and a methyne carbon at ca. 39.2 ppm in isomers (p) and (r) vs. 39.7 ppm in isomers (g) and (s).

EXAMPLE 8

3aα,7aα-Octahydro-1S,1α-methyl-4α,7α-methano-2H-inden-2-one, (+b). The 851 mg (92% (p)) was dissolved in 15 mL of MeOH. A solution of 800 mg of oxalic dihydrate in 2 mL of water was added. From time to time as the cloudiness cleared water was added until a total of 5 mL had been added. The mixture was stirred for 18 h more diluted with water and extracted with hexane (3X) washing with 5% NaHCO₃, water and brine. After drying over sodium sulfate and evaporation, Flash Chromatography (hexane-EtOAc 19:1) provided 460 mg (78%, 84% ee) of (+b), $[\alpha]_D+21.2°$ (1.118% hexane).

EXAMPLE 9

3aα,7aα-Octahydro-1R,1α-methyl-4α,7α-methano-2H-inden-2-one, (−b). The 271 mg (95% r) was dissolved in 15 mL of MeOH and a solution of 400 mg of oxalic acid dihydrate in 5 mL of water was added. After stirring at room temperature for 18 h, the mixture was diluted with water and extracted 3X hexane, washing with 5% NaHCO₃, water and brine. After drying over sodium sulfate and evaporation the residue was chromatographed (Flash, hexane-EtOAc 19:1) to provide 154 mg (82%, 90% ee) of (−b), $[\alpha]_D−21.2°$ (0.998% hexane).

EXAMPLE 10

4aα,8aα-Octahydro-1S,1α-methyl-5α,8α-methano-3H-2-benzopyran-3-one, (−f). To a solution of 460 mg (2.8 mmole) of (+b) in 6 mL of dry methylene chloride was added 950 mg (807 mg, 4.6 mmole) of 85% m-chloroperoxybenzoic acid. After two days the solids were removed by filtration and rinsed with hexane. The filtrate was washed with sodium bicarbonate, water and brine. After evaporation of solvents chromatography (Flash, hexane-EtOAc 98:2) provided 343 mg (68%) of (−f). Crystallization from a small amount of hexane provided a solid melting at 42°–44°, $[\alpha]_D−99.7°$ (0.954% hexane).

EXAMPLE 11

4aα,8aα-Octahydro-1R,1α-methyl-5α,8α-methano-3H-2-benzopyran-3-one, (+f). To a solution of 132 mg (0.8 mmole) of (−b) in 4 mL of dry methylene chloride was added 210 mg (178 mg, 1.03 mmole) of 85% m-chloroperoxybenzoic acid. After two days the solids were removed by filtration and rinsed with hexane. The filtrate was washed with sodium bicarbonate, water and brine. After evaporation of solvents chromatography (Flash, hexane EtOAc 98:2) provided 132 mg (91%) of (+f). Crystallization from a small amount of hexane provided solid melting at 43°–44°, $[\alpha]_D+105.1°$ (0.969% CH₂Cl₂.

EXAMPLE 12

4aα,8aα-Octahydro-1S,1α-methyl-5α,8α-methano-1H-2-benzopyran-3-ol, (−g). A solution of 343 mg (1.9 mmole) of (−f) in 10 mL of toluene was chilled in a −78° bath and 4 mL of 1 M DIBAL in toluene was added and stirred at −78° for 2 h. The mixture was quenched cautiously with 2 mL of MeOH. After warming to room temperature, 30 mL more MeOH was added. The solid was removed by filtration, rinsing thoroughly with MeOH. The filtrate was evaporated, and the residue was chromatographed (Flash, hexane-EtOAc 3:2) to provide 316 mg (91%) of (−g), $[\alpha]_D−31.3°$ (1.032% hexane). Crystallization from a small amount of hexane provided 19 mg of racemic (g), m.p. 96°–97°. The enriched filtrate amounted to 278 mg (−g) (ca. 90% ee).

EXAMPLE 13

4aα,8aα-Octahydro-1R,1α-methyl-5α,8α-methano-1H-2-benzopyran-3-ol, (+g). A solution of 95 mg (0.52 mmole) of (+f) in 5 mL of toluene was chilled in a −78° bath and 2 mL of 1 M DIBAL in toluene was added and stirred at −78° for 2 h. The mixture was quenched cautiously with 1 mL of MeOH. After warming to room temperature, 20 mL more MeOH was added. The solid was removed by filtration, rinsing thoroughly with MeOH. The filtrate was evaporated, and the residue was chromatographed (Flash, hexane-EtOAc 3:2) to provide 74 mg (77%) of (+g), $[\alpha]_D+34.8°$ (0.705% hexane).

EXAMPLE 14

7-(3α-Acetyl-1S,1α,4α-bicyclo[2.2.1]hept-2β-yl)-5Z-heptenoic acid, (+n). To a suspension of 2.23 g (5.03 mmole) freshly crushed and dried (60°, high vac) (4-carboxybutyl)triphenylphosphonium bromide in 10 mL dry THF was added 10 ml of 1 M sodium (bistrimethylsilyl)amide in THF. The mixture was stirred at room temperature for 18 h under nitrogen, cooled in an ice bath and then a solution of 278 mg (1.52 mmole) of (−g) in 50 mL of THF was added over 10 min. The ice bath was removed and the mixture was stirred 2 h. After the addition of 25 mL of 5% NaHCO₃ the mixture was extracted with ether. The aqueous layer was acidified with 10% HCl and extracted twice with ether washing with water and brine. After being dried over sodium sulfate the solvents were evaporated and the residue was chromatographed on a short acidic silica column (hexane-EtOAc, 4:1) to provide 440 mg of a crude product which was dissolved in 20 mL of acetone, chilled in an ice bath and treated with a slight excess of Jones reagent. The mixture was dissolved in 30 mL of water and extracted with ether. After washing with water and brine followed by drying over sodium sulfate the solvents were evaporated and the residue was dissolved in 2 mL of 1 N NaOH and stirred at room temperature for 1 hr. After acidification with 10% HCl the product was extracted with ether which was washed with water and brine and dried over sodium sulfate. After evaporating solvents chromatography on a short acidic silica column (hexane-EtOAc 4:1) provided 255 mg (63%) of a mixture, $[\alpha]_D+22.6°$ (1.062% hexane), containing ca. 90% (+n) and 10% (q).

EXAMPLE 15

7-(3α-Acetyl-1R,1α,4α-bicyclo[2.2.1]hept-2β-yl)-5Z-heptenoic acid, (−n). To a suspension of 1.0 g (2.31 mmole) freshly crushed and dried (60°, high vac) (4-carboxybutyl)triphenylphosphonium bromide in 5 mL dry THF was added 4.6 mL of 1 M sodium (bistrimethylsilyl)amide in THF. The mixture was stirred at room temperature for 1 h under nitrogen, cooled in an ice bath and then a solution of 60 mg (0.33 mmole) of (+g) in 5 mL of THF was added. The ice bath was removed and the mixture was stirred 2 h. After the addition of 25 mL of 5% $NaHCO_3$ the mixture was extracted with ether. The aqueous layer was acidified with 10% HCl and extracted twice with ether washing with water and brine. After being dried over sodium sulfate the solvents were evaporated and the residue was chromatographed on a short acidic silica column (hexane-EtOAc, 4:1) to provide 70 mg of a crude product which was dissolved in 10 mL of acetone, chilled in an ice bath and treated with a slight excess of Jones reagent. The mixture was diluted in 20 mL of water and extracted with ether. After washing with water and brine followed by drying over sodium sulfate the solvents were evaporated and the residue was dissolved in 1 mL of 1 N NaOH and stirred at room temperature for 1 hr. After acidification with 10% HCl the product was extracted with ether which was washed with water and brine and dried over sodium sulfate. After evaporating solvents chromatography on a short acidic silica column (hexane-EtOAc 4:1) provided 47 mg (53%) of a mixture containing ca. 90% (−n) and 10% (p).

EXAMPLE 16

7-[3α-[[(Phenylamino)thioxomethyl]hydrazono]ethyl]-1S, 1α,4α-bicyclo-[2.2.1]hept-2β-yl]-5Z-heptenoic acid, SC 46985. A solution of 248 mg (0.94 mmole) of the mixture of (+n) and (q) and 350 mg (2.1 mmole) of 4-phenyl-3-thiosemicarbazide in 1.0 mL of pyridine was stirred at room temperature for 20 h. A solution of the mixture in 20 mL of methylene chloride was washed twice 20 mL 5% HCl, water and brine. After drying over sodium sulfate and evaporation of solvent the residue was chromatographed on an acidic silica column (hexane-EtOAc, 4:1) to provide 328 mg. (85%) of (+r) (90% ee) containing about 10% of its 5E isomer, (+s).

EXAMPLE 17

7-[(3α-[[(Phenylamino)thioxomethyl]hydrazono]ethyl]-1R, 1α,4α-bicyclo[2.2.1]hept 2β-yl)]-5Z -heptenoic acid, SC-46984. A solution of 47 mg (0.18 mmole) of the mixture of (−n) and (p) and 60 mg (0.36 mmole) of 4-phenyl-3-thiosemicarbazide in 0.5 mL of pyridine was stirred at room temperature for 28 h. A solution of the mixture in 20 mL of methylene chloride was washed twice 20 mL 5% HCl, water and brine. After drying over sodium sulfate and evaporation of solvent the residue was chromatographed on an acidic silica column (hexane EtOAc, 4:1) to provide 72 mg. (97%) of (−r) (9% ee) containing about 10% of its 5E isomer, (−s).

CHIRAL TEMPLATE BASED SYNTHESIS

EXAMPLE 18

3aR,3aα,7aα-Octahydro-4α,7α-methano-1H-inden-1-one, (+v). A solution 5.65 g of 3aS,3aα,4,7,7aα-tetrahydro-4α,7α-methano-1H-inden-1-one[2], (+u), in 50 mL THF was hydrogenated over a small amount of W-2 Raney Nickel at atmospheric pressure and 25° C. over 2 h. After removing the catalyst and distillation of the solvent Flash chromatography (hexane-ether 4:1) provided 5.21 g (90%) of (+v), a waxy solid, $[\alpha]_D+260.5°$ (0.925% hexane) followed by a small amount of an over reduction product.

EXAMPLE 19

3aS,3aα,4,5,6,7,7aα-Hexahydro-4α,7α-methano-1H-inden-3-yl trifluoromethanesulfonate, (−w) by the method of McMurray and Scott (References 3 and 4). To a solution of 6.2 mL (5.32 g, 37.7 mmoles) of N-isopropylcyclohexylamine in 30 mL of THF at −78° C. was added 26.45 mL (37.8 mmoles) of 1.43 M n-butyllithium in hexane. After stirring for 45 min, a solution of 5.11 g (34.1 mmoles) of (+v) in 25 mL THF was added. After 2 h at −78° C. a solution of 13.51 g (37.8 mmoles) of N-phenyltrifluoromethanesulfonimide in 40 mL THF was added and mixture was stirred at 0° for 16 h. After the addition of 50 mL water, the product was extracted with hexane washing with water and brine. After evaporating solvents the residue was chromatographed (Flash, hexane) to provide 5.71 g of crude (−w), $[\alpha]_D$ −14.6° (1.012% hexane).

EXAMPLE 20

3aS,3aα,4,5,6,7,7aα-Hexahydro-3-methyl-4α,7α-methano-1H-indene, (y) by the method of McMurray and Scott (References 3 and 4). To a slurry of 7.26g (38.1 mmoles) of copper iodide in 25 mL ether at −78° was added 64.6 mL (76.2 mmoles) of 1.18 M methyllithium-lithium bromide complex in ether. After warming to −30° a solution of 9.0 g (31.8 mmoles) (w) in 5 mL of ether was added. The mixture was maintained at −20° for 20 h and then 5 mL of methyl iodide was added. After being warmed to 20°, 100 mL saturated $NH_4Cl$ and a small amount of $NH_4OH$ were added. After being stirred at room temperatures for 20 h, the mixture was extracted with hexane, washed with water and brine, and dried over sodium sulfate. After concentrating the solution, chromatography (Flash, hexane) provided 4.17 g of a mixture of (y) and 3aS,3aα,4,5,6,7,7aα-hexahydro-4α,7α-methano-1H-indene, (x), (4:1).

EXAMPLE 21

3aβ,7aβ-Octahydro-1R,1α-methyl-2β-hydroxy-4β,7β-methano-2H-indene, (z). To a solution of 4.17 g of the crude mixture of (y) and (x) in 30 mL THF at 0° was added 20 mL of 2M borane-methyl sulfide complex in THF. The mixture was allowed to warm to room temperature and stirred for 3 h After again cooling to 0°, 10 mL water and 40 mL IN NaOH were added followed by 20 mL 30% hydrogen peroxide. The mixture was allowed to warm to room temperature and stirred for 45 min more. After the addition of 50 mL 20% sodium carbonate solution the products were extracted with ether, washing with water and brine. After drying over sodium sulfate, solvents were evaporated and the residue amounted to 5.16 g of crude (z).

EXAMPLE 22

3aβ,7aβ-Octahydro-1R,1α-methyl-4β,7β-methano-2H-inden-2-one, (+e). The 5.16 g of crude (z) (above) was dissolved in 50 mL acetone and chilled in an ice bath. Jones reagent was added until a slight excess persisted (ca. 10 mL). After dilution with 200 mL water, the mixture was extracted with ether, washing water, 5% sodium bicarbonate and brine. After removing solvents chromatography (Flash, hexane-ether 98:1) provided 2.35 g of (+e), $[\alpha]_D +20.2°$ (1.107% hexane), as the first material eluted. This was followed by a mixture of (v) and (a). Preparation of a ketal with (2R,3R)-2,3-butanediol as above provided a above provided a sample which contained only ketal (g) by $^{13}C$ NMR analysis.

EXAMPLE 23

4aβ,8aβ-Octahydro-1R,1α-methyl 5β,8β-methano-3H-2-benzoyran-3-one, (bb). A solution of 1.53 g (9.4 mmoles) of (+e) and 2.47 g (12 mmoles) 85% m-chloroperoxybenzoic acid in 20 mL methylene chloride was stirred at room temperature for 5 days. The solid was removed by filtration, rinsing well with hexane. The filtrate was evaporated and the residue chromatographed (Flash, hexane-EtOAc 9:1–4:1) to provide 0.38 g (25%) of recovered (+e) followed by 0.74 g (44%) of (bb).

EXAMPLE 24

4aβ,8aβ-Octahydro1R,1α-methyl-5β,8β-methano-1H-2-benzopyran-3-ol, (cc). To a solution of 740 mg (4.11 mmoles) of (bb) in 5 mL toluene at −78° was added 10.3 mL 1 M diisobutylaluminum hydride in toluene. After 4 h at −78°, 30 mL MeOH was added and the mixture was allowed to room temperature. After 2 h the solids were removed by filtration rinsing thoroughly with MeOH. The filtrate was evaporated and the residue chromatographed (Flash, hexane EtOAc 7:3) to provide 620 mg (83%) of (cc).

EXAMPLE 25

7-[3β-(1S*-Hydroxyethyl)-1R,1α,4α-bicyclo[2.2.1]hept-2β-yl]-5Z-heptenoic acid, (dd) and 7-[3β-(1S* hydroxyethyl)-1R,1α,4α-bicyclo[2.2.1]hept-2β-yl]-5E-heptenoic acid, (ee). To a suspension of 3.02 g (6.8 mmoles) (4-carboxybutyl)triphenylphosphonium bromide in 20 mL THF was added 13.6 mL 1 M sodium bis(trimethylsilyl) amide in THF. After 18 h stirring at room temperature, the mixture was cooled in an ice bath and a solution of 0.62 g (3.4 mmoles) of (cc) in 20 mL THF was added. After 4 h the mixture was allowed to warm to room temperature for 20 h more and then 20 mL water was added. The aqueous layer was separated and acidified with 10% HCl. The products were extracted with ether, washing with water and brine. After drying over sodium sulfate and evaporation, repeated low pressure liquid chromatography (Woelm pH controlled silica, hexane EtOAc 3:2) provided first 70 mg (8%) of (ee) followed by 400 mg (44%) of (dd).

EXAMPLE 26

7-(3α-Acetyl-1R,1α,4α-bicyclo[2.2.1]hept-2β-yl)-5Z-heptenoic acid, (−n). A solution of 400 mg (1.5 mmoles) of (dd) in 12 mL acetone was chilled in an ice bath and about 1 mL of Jones reagent was added until a slight excess persisted. After dilution with 20 mL water extraction with ether, washing with water and brine and drying over sodium sulfate, evaporation of solvents left a residue of 380 mg. This material was dissolved in 15 mL 1N NaOH. After 1 h at room temperature the solution was acidified with 10% HCl and extracted with ether washing with water and brine. Chromatography on acidic silica (hexane-EtOAc 4:1) provided 160 mg (40%) of (−n).

EXAMPLE 27

7-(3α-Acetyl-1R,1α,4α-bicyclo[2.2.1]hept-2β-yl)-5E-heptenoic acid, (p). A solution of 70 mg (0.26 mmole) of (ee) in 3 mL acetone was chilled in an ice bath and titrated with Jones reagent (ca. 0.08 mL). After dilution with water and ether extraction, washing with water and brine, drying over sodium sulfate and evaporation left a residue of 80 mg. This material was dissolved in 1.5 mL 1 N NaOH. After 1 h at room temperature the solution was acidified with 5% HCl and the product extracted with ether washing with water and brine. After drying over sodium sulfate and evaporation of solvents, chromatography on acidic silica gave 40 mg (58%) of (p).

EXAMPLE 28

7-[3α-[1-[[(Phenylamino)thioxomethyl]hydrazono]ethyl]-1R, 1α,4α-bicyclo-[2.2.1]hept-2β-yl]-5Z-heptenoic acid, SC-46984. A solution of 140 mg (0.53 mmole) of (−n) and 106 mg (0.64 mmole) of 4-phenyl-3-thiosemicarbazide in 0.6 mL of pyridine was stirred at room temperature for 20 h. A solution of the mixture in 20 mL of methylene chloride was washed twice 20 mL 5% HCl, water and brine. After drying over sodium sulfate and evaporation of solvent the residue was chromatographed on acidic silica column (hexane-EtOAc 4:1) to provide 160 mg (73%) of (−n).

EXAMPLE 29

7-[3α-[1-[[(Phenylamino)thioxomethyl]hydrazono]ethyl]-1R, 1α,4α-bicyclo-[2.2.1]hept-2β-yl]-5E-heptenoic acid, SC-47721. A solution of 40 mg (0.15 mmole) of (p) and 30 mg (0.18 mmole) of 4-phenyl-3-thiosemicarbazide in 0.4 mL of pyridine was stirred at room temperature for 20 h. A solution of the mixture in 20 mL of methylene chloride was washed twice 20 mL 5% HCl, water and brine. After drying over sodium sulfate and evaporation of solvent the residue was chromatographed on acidic silica column (hexane-EtOAc 4:1) to provide 40 mg. (64%) of (−s).

EXAMPLE 30

3aS,3aα,7aα-Octahydro-4α,7α-methano-1H-inden-1-one, (−v). A solution of 1.22 g of 3aR,3aα,4,7,7aα-tetrahydro-4α,7α-methano-1H-inden-1-one, (−u), in 20 mL THF was hydrogenated over a small amount of W-2 Raney Nickel at atmospheric pressure and 25° C. over 2 h. After removing the catalyst and distillation of the solvent the residue, 1.24 g (99%) of (−v), $[\alpha]_D -251.7°$ (1.408% hexane), was free of any other material which could be detected by TLC or NMR.

EXAMPLE 31

3aR,3aα,4,5,6,7,7aα-Hexahydro-4α,7α-methano-1H-inden-3-yl trifluoromethanesulfonate, (+w). To a solution of 1.8 mL (1.54 g, 10.9 mmoles) of N-isopropylcyclohexylamine in 10 mL of THF at −78° C. was added 6.5 mL (10.3 mmoles) of 1.53 M n-butyllithium in hexane. After stirring for 30 min, a solution of 1.20 g (8.0 mmoles) of (−v) in 10 ml THF was added. After 30 min at −78° C. a solution of 3.80 g (10.6 mmoles) of N-phenyltrifluoromethanesulfonimide in 10 mL THF was added and mixture was stirred at 0° for 2 h. After the addition of 20 mL water, the product was extracted with hexane washing with water and brine. After evaporating solvents the residue was chromatographed (Flash, hexane) to provide 1.95 g of crude (+w).

EXAMPLE 32

3aR,3aα,4,5,6,7,7aα-Hexahydro-3-methyl-4α,7α-methano-1H-indene, (ii). To a slurry of 1.57 g (8.2 mmoles) of copper iodide in 5 mL ether at −78° was added 14 mL (16.5 mmoles) of 1.18 M methyllithium-lithium bromide complex in ether. After warming to −25° a solution of 1.95 g (6.9 mmoles) (+w) in 5 mL of ether was added. The mixture was maintained at −20° for 20 h and then 1 mL of methyl iodide was added. After being warmed to 20°, 10 mL saturated NH$_4$Cl and a small amount of NH$_4$OH were added. After being stirred at room temperature for 20 h, the mixture was extracted with hexane, washed with water and brine, and dried over sodium sulfate. After concentrating the solution, chromatography (Flash, hexane) provided 650 mg of a mixture of (ii) and 3aR,3aα,4,5,6,7,7a-hexahydro-4α,7α-methano-1H-indene, (hh) (4:1).

EXAMPLE 33

3aβ,7aβ-Octahydro-1S-1α-methyl-2β-hydroxy-4β,7β-methano-2H-indene, (jj). To a solution of 650 mg of the crude mixture of (ii) and (hh) in 10 mL THF at 0° was added 3 mL of 2M borane-methyl sulfide complex in THF. The mixture was allowed to warm to room temperature and stirred for 18 h. After again cooling to 0°, 1 mL water and 4 mL 1 N NaOH were added followed by 3 mL 30% hydrogen peroxide. The mixture was allowed to warm to room temperature and stirred for 30 min more. After the addition of 10 mL 20% sodium carbonate solution the products were extracted with ether, washing with water and brine. After drying over sodium sulfate, solvents were evaporated and the residue chromatographed (Flash, hexane-EtOAc 4:1) to provide 462 mg of (jj), followed by 123 mg of a crude mixture.

EXAMPLE 34

3aβ,7aβ-Octahydro-1S-1α-methyl-4β,7β-methano-2H-inden-2-one, (−e). The 462 mg of (jj) (above) was dissolved in 20 mL acetone and chilled in an ice bath. Jones reagent was added until a slight excess persisted. After dilution with 50 mL water, the mixture was extracted with ether, washing water, 5% sodium bicarbonate and brine. After removing solvents chromatography (Flash, hexane-ether 98:1) provided 330 mg of (−e). Preparation of a ketal with (2S,3S)-2,3-butanediol as above provided a sample containing only ketal (w) by $^{13}$C NMR analysis.

EXAMPLE 35

3aα,7aα-Octahydro-1S-1α-methyl-4α,7α-methano-2H-inden-2-one. (+b). A solution of 278 mg of (−e), 1 mL 2,3 butanediol and 5 mg camphorsulfonic acid in 25 mL benzene was refluxed under a Dean Starke trap for 40 h. After adding 0.5 mL Et$_3$N and concentrating the residue was passed through a short Flash column with hexane to provide a total ketal fraction of 387 mg. This material and 400 mg oxalic acid dihydrate were stirred in 10 mL MeOH and 2 mL water for 20 h. After dilution with 20 mL 5% NaHCO$_3$, the mixture was extracted with hexane, washing with 5% NaHCO$_3$, water and brine. After removing solvents the residue consisted of 240 mg of (+b).

EXAMPLE 36

4aα,8aα-Octahydro-1S-1α-methyl-5α,8α-methano-3H-2-benzopyran-3-one, (−f) To a solution of 240 mg (1.46 mmole) of (+b) in 10 mL of dry methylene chloride was added 500 mg (425 mg, 2.4 mmole) of 85% m-chloroperoxybenzoic acid. After 40 h the solids were removed by filtration and rinsed with hexane. The filtrate was washed with sodium bicarbonate, water and brine. After evaporation of solvents chromatography (Flash, hexane-Et$_2$O 4:1) provided 257 mg (98%) of (−f)

EXAMPLE 37

4aα,8aα-Octahydro-1S-1α-methyl-5α,8α-methano-1H-2-benzopyran-3-ol, (−g). A solution of 257 mg (1.43 mmole) of (−f) in 8 mL of toluene was chilled in a −78° bath and 2.5 mL of 1 M DIBAL in toluene was added and stirred at −78° for 2 h. The mixture was quenched cautiously with 5 mL of MeOH. After warming to room temperature, 20 mL more MeOH was added. The solid was removed by filtration, rinsing thoroughly with MeOH. The filtrate was evaporated, and the residue was chromatographed (Flash, hexane EtOAc 3:2) to provide 258 mg (99%) of (−g).

EXAMPLE 38

7-(3α-Acetyl-1S,1α,4α-bicyclo[2.2.1]hept-2β-yl)-5Z-heptenoic acid, (+n). To a suspension of 1.25 g (2.83 mmole) freshly crushed and dried (4-carboxybutyl)triphenylphosphonium bromide in 10 mL dry THF was added 5.7 mL of 1 M sodium (bistrimethylsilyl)amide in THF. The mixture was stirred at room temperature for 18 h under nitrogen, cooled in an ice bath and then a solution of 258 mg (1.42 mmole) of (−g) in 50 mL of THF was added over 10 min. The ice bath was removed and the mixture was stirred 2 h. After the addition of 25 mL of 5% NaHCO$_3$ the mixture was extracted with ether. The aqueous layer was acidified with 10% HCl and extracted twice with ether washing with water and brine. After being dried over sodium sulfate the solvents were evaporated and the residue was chromatographed on a short acidic silica column (hexane-EtOAc, 4:1) to provide 350 mg of a crude product which was dissolved in 10 mL of acetone, chilled to −10° and treated with a slight excess of Jones reagent. The mixture was dissolved in 30 mL of water and extracted with ether. After washing with water and brine followed by drying over sodium sulfate the solvents were evaporated and the residue was dissolved in 6.2 mL of 1 N NaOH and stirred at room temperature for 4 h. After acidification with 10% HCl the product was extracted with ether which was washed with water and brine and dried over sodium sulfate. After evaporating solvents chromatography on a short acidic silica column (hexane-EtOAc 4:1) provided 250 mg (67%) of a mixture, containing ca. 90% (+n) and 10% (q).

EXAMPLE 39

Methyl 7-(3α-Acetyl-1S,1α,4α-bicyclo[2.2.1]hept-2β-yl)-5Z-heptenoate, (11). A solution of 250 mg of the mixture of (+n) and (q) in 10 mL ether was chilled in an ice bath and treated with a slight excess of ethereal diazomethane. After adding a few drops of acetic acid, the mixture was washed with 5% sodium bicarbonate and brine and then dried over sodium sulfate. After removing solvents, the residue was chromatographed (Flash, methylene chloride-acetone 99:1) to provide 160 mg of a mixture. Further chromatography (LPLC Woelm pH controlled Silica, methylene chloride-acetone 199:1) gave a partial separation providing first 27 mg of (ll) followed by 85 mg of a mixture of this and the 5E isomer (mm).

EXAMPLE 40

7-(3α-Acetyl-1S,1α,4α-bicyclo[2.2.1]hept-2β-yl)-5Z-heptenoic acid, (+n). A solution of 27 mg of (ww) in 0.2 mL MeOH was chilled in an ice bath and 0.16 mL 1 N NaOH was added. After being stirred for 20 h, the mixture was evaporated under a nitrogen stream and the residue in water was acidified with 5% HCl. The mixture was extracted with ether followed by washing with water and brine. After being dried over sodium sulfate, evaporation of solvents left 20 mg of (+n).

EXAMPLE 41

7-[3α-[[(Phenylamino)thioxomethyl]hydrazono]ethyl]-1S, 1α,4α-bicyclo-[2.2.1]hept-2β-yl]-5Z-heptenoic acid, SC-46985. A solution of 20 mg of (+n) and 16 mg of 4-phenyl-3-thiosemicarbazide in 0.2 mL of pyridine was stirred at room temperature for 20 h. After dilution with 10 mL of methylene chloride the mixture was washed with 5% HCl, water and brine. After drying over sodium sulfate and evaporation of solvent the residue was chromatographed on an acidic silica column (hexane-EtOAc 4:1) to provide 22 mg. of (+r).

REFERENCES

1. Brown, H. C.; Rothberg, I.; Vander Jagt, D. L., *J Org. Chem.* 1972, 37, 4098–4100.
2. Klunder, A. J. H.; Huizinga, W. B.; Hulshof, A. J. M., Zwanenburg, B., *Tetrahedron Letters* 1986, 27, 2543–2546.
3. Mc Murry, J. E.; Scott, W. J., *Tetrahedron Letters* 1983, 24, 979–982.
4. Mc Murry, J. E.; Scott, W. J., *Tetrahedron Letters* 1980, 21, 4313–4316.

PHARMACOLOGIC ACTIVITY

Methods:

I. In Vitro a. Inhibition of U-46619-induced platelet aggregation (rat)

Platelet rich plasma (PRP) was prepared from heparanized whole blood (5 units/ml) drawn from the abdominal aorta of ether anesthetized rats. PRP was prepared by centrifugation (Sorvall RC2B, DuPont, Wilmington, Del.) of the whole blood at 150×g for 10 min. Platelet poor plasma (PPP) was prepared by centrifugation at 1200×g for 20 min. Aliquots of PRP and PPP were used to standardize the aggregometer (Payton, Buffalo, N.Y., model 300B) with the recorder (Riken Denshi 2 channel recorder, Payton, model SP-H5P) for measurement of minimum and maximum light transmittance, respectively.

Platelet aggregation was measured as an increase in light transmittance. PRP (390 μl aliquot 5 μl compound vehicle) was preincubated for 1 min. at 37° C., with stirring at 900 rpm in the aggregometer.

The vehicle control response was obtained by adding U-46619 (Cayman Chemical, Ann Arbor, MI, 1-2 units/cuvette/10 μl) to the aliquot of PRP. Aggregation was monitored until maximum aggregation was achieved (approximately 3 min. following the addition of U-46619). Amount of aggregation was measured by grids on the strip chart.

Compounds were dissolved in either ethanol (ETOH) or $Na_2CO_3$ (0.1 M) and preincubated at the desired concentration in PRP for 1 min. at 37° C. with stirring. At the end of the preincubation, U-46619 was added and aggregation measured. Inhibition of aggregation by compound was calculated as percent inhibition of the control aggregation response to U-46619. Dose response curves were generated and $IC_{50}$'s calculated by linear regression.

b. Analysis of partial agonism with SC-46985 (human washed platelets)

Sixty ml of blood were drawn into 1/10 volume of CCD (100 mM Na Citrate and 136 mM glucose, pH 6.5 with HCl) and PRP prepared as described above. PRP was placed on ice for 15 min. One half of the volume of CCD was added and recentrifuged. The platelet pellet was gently resuspended in ½ the original volume of PRP in a 0° C. modified Tangen-Hepes-BSA buffer (145 mM NaCl, 5 mM KCl, 0.05 mM $CaCl_2$, 0.1 mM $MgCl_2$, 11 mM glucose, 15 mM Hepes, 1 mg/ml bovine serum albumin, pH adjusted to 7.4 with NaOH). The resuspended platelets were incubated undisturbed at 37° C. for 30 min. After incubation a platelet count was determined and adjusted to $3\times10^8$ cells/ml with the Tangen-Hepes-BSA buffer.

425 μl of the washed human platelet suspension was incubated in the aggregometer in the presence of 16 mM $CaCl_2$ (50 μl) and SC-46985 for 5 and 10 min. Baseline aggregation was observed to determine any compound related shape change. (In a study similar to (a) above, aliquots of human washed platelets were incubated with various concentrations of SC-46985 and U-46619 to determine dose-related inhibition of aggregation).

c. Inhibition of collagen induced platelet aggregation in dogs by SC-44161 and SC-46984

Blood was collected into citrated vacutainers from the jugular veins of conscious dogs and centrifuged at 200×g for 7 min. PRP was separated and an aliquot (450 μl) incubated 1 min. in the aggregometer (as described above). Collagen (50 μl, Helena Reagent, bovine tendon) was added and aggregation monitored for 5 min. Percent inhibition and $IC_{50}$'s were determined as previously described.

II. Ex vivo—(rat) Inhibition of U-46619 induced platelet aggregation a. Intravenous Rats were anesthetized with ether and the jugular vein exposed. Compound dissolved in 0.1 M Na Carbonate was injected as a bolus into the jugular vein. Blood (5 ml, heparanized) was sampled 30 sec. later from the abdominal aorta. PRP was prepared by quick centrifugation (Eppendorf, model 5415 at 12,000 rpm for 5 sec. PPP was prepared by centrifugation for 2 min. PRP was diluted 1:1 with PPP from similarly treated animals. Aggregation was monitored for 5 min. and inhibition was determined as previously described.

b. Intragastric

Compounds dissolved in Na Carbonate were administered to conscious rats with an I.G. tube. Fifteen minutes post administration (time previously determined to show maximum effect), rats were anesthetized with ether and blood was sampled from the abdominal aorta. PRP was prepared as described in II a.

Results:

I. In Vitro a. Inhibition of U-46619 induced platelet aggregation (rat)

Results of in vitro studies in rat PRP with the compounds in two vehicles, ETOH and Na Carbonate, are reported in Table I. SC-44161 (racemic) was 5-10 fold more potent when in aqueous solution than when dissolved in ethanol. SC-46984, the cis isomer of the active enantiomer, was 10-50 times more potent in aqueous solution than in ethanol, and approximately 100 times more potent than SC-44161. The trans form of the active enantiomer, SC-47721, was less potent than SC-46984 but still 10-50 times more potent than SC-44161 .

b. Analysis of partial agonism with SC-4698 (human)

SC-46985 was incubated with washed human platelets in an attempt to detect potential partial agonist activity. After 5 and 10 min. incubation, there was no evidence of shape change or aggregation, indicating a lack of partial agonist activity. (When aliquots of platelets were incubated with SC-46985 and stimulated with U-46619, an IC$_{50}$ of $5.6 \times 10^{-6}$ M was determined.)

c. Inhibition of collagen induced platelet aggregation by SC-44161 and SC-46984

The IC$_{50}$'s for inhibition of collagen induced aggregation by SC-44161 and SC-46984 in dog PRP were $1.14 \times 10^{-5}$ M and $2.09 \times 10^{-6}$ M, respectively.

II. Ex vivo—Inhibition of U-46619 induced aggregation a. Intravenous

Figure I shows the data obtained when rats were intravenously injected with SC-44161, SC-46984 and SC-46985. In this model, SC-44161 had an ED$_{50}$ of 31 μg/kg. The two enantiomers of SC-44161, (SC-46984 and SC-46985) were tested in the same model for comparison. SC-46984 has an ED$_{50}$ of 8.7 μg/kg (approximately 3.5 times more potent than SC-44161) while SC-46985 had an ED$_{50}$ of 45 μg/kg (approximately 1.5 times less potent than SC-44161).

b. Intragastric

The potency of SC-44161 was determined when compound was administered I.G. and compared with SC-46984 and SC-47721 (FIG. 2). SC-44161 had an I.G. ED$_{50}$ of 1.21 mg/kg. In the same model SC-46984 had an I.G. ED$_{50}$ of 0.44 mg/kg (approximately 2.8 times more potent than SC-44161). For comparison SC-47721 was tested at 1 mg/kg and gave 37.5% inhibition at that dose.

c. I.G./I.V. ratio

From the I.V. and the I G. studies, an I.V./I.G. ratio was calculated. For SC-44161 the I.V./I.G. ratio was 39 and for SC-46984 the ratio was 51. This difference in I.V./I.G. ratios is probably not large enough to be important.

TABLE I

INHIBITION OF U-46619 INDUCED AGGREGATION IN VITRO IN RAT PLATELET RICH PLASMA

| COMPOUND | IC$_{50}$ (M) | |
|---|---|---|
| | ETOH | Na$_2$CO$_3$ |
| SC-44161 | $2.6 \times 10^{-7}$ | $7.0 \times 10^{-8}$ |
| SC-46984 | $5.0 \times 10^{-8}$ | $7.0 \times 10^{-10}$ |
| SC-46985 | $9.7 \times 10^{-7}$ | $\sim 2.5 \times 10^{-6(a)}$ |
| SC-46986 | $6.9 \times 10^{-7}$ | N.D. |
| SC-47721 | N.D. | $\sim 7.5 \times 10^{-9(a)}$ |

[a] In Na$_2$CO$_3$ the dose response curves were so steep that the values of relative potency (IC$_{50}$'s) are estimates based on the all-or-none responses.
N.D. = not done CHART 1
INHIBITION OF U-46619 INDUCED PLATELET AGGREGATION BY SC-44161, SC-46984 AND SC-46985 (I.V.)

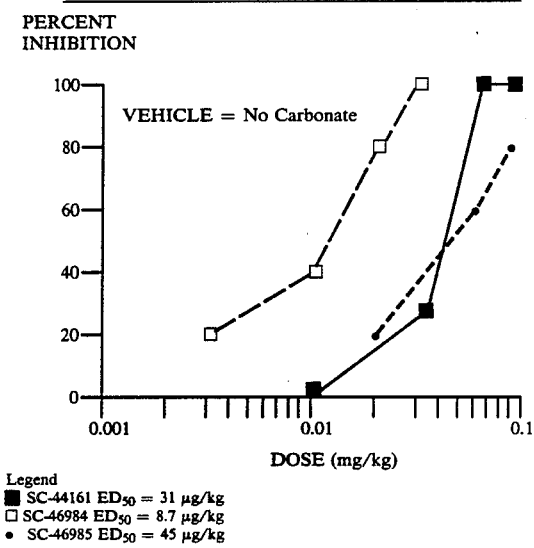

Legend
■ SC-44161 ED$_{50}$ = 31 μg/kg
□ SC-46984 ED$_{50}$ = 8.7 μg/kg
● SC-46985 ED$_{50}$ = 45 μg/kg CHART 2
INHIBITION OF U-46619 INDUCED PLATELET AGGREGATION BY SC-44161, SC-46984 AND SC-47721 (I.G.)

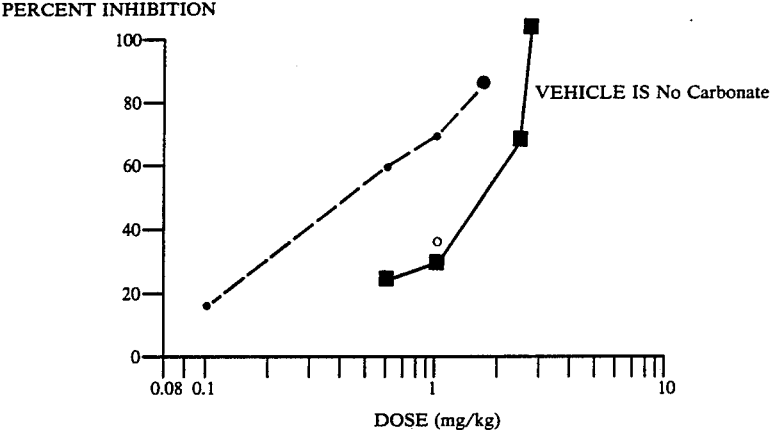

Legend
■ SC-44161 ED$_{50}$ = 1.21 mg/kg g/kg 50%
● SC-46984 ED$_{50}$ = 0.44 mg/kg
○ SC-47721 (1 mg/kg)

What is claimed is:

1. A method of making an optically active compound of the formula:

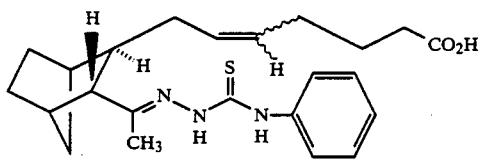

or

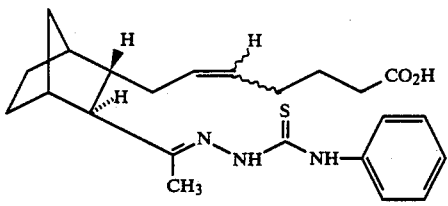

or a pharmaceutically acceptable salt thereof, which compound or salt thereof can be either the cis or the trans geometric isomer, said method comprising the steps of (a) resolving a compound of the formula:

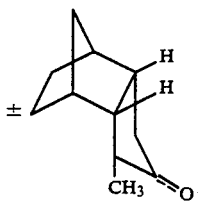

into the respective diastereoisomers of the formulae

III and

IV by reacting the compound of formula II with a diol whose hydroxyl functions are attached to adjacent chiral carbon atoms having symmetry element defining C$_2$ symmetry:

(b) hydrolyzing the product of (a);
(c) oxidizing the product of (b) by peracid oxidation using a peracid as oxidizing agent;
(d) reducing the product of (c);
(e) oxidizing the product of (d) and isomerizing the resultant product with base to provide a methyl ketone;
(f) reacting the methyl ketone product of (e) with 4-phenyl-3-thiosemicarbazide; and where appropriate
(g) forming a pharmaceutically acceptable salt of the product of (f).

2. A method according to claim 1, wherein the diol is selected from the group consisting of (2R,3R)-2,3-butanediol and (2S,3S)-2-butanediol.

3. A method of making optically active compounds of formula:

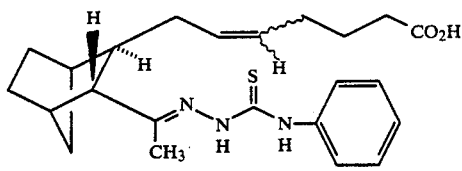

or a pharmaceutically acceptable salt thereof, which compound or salt thereof can be either the cis or the trans geometric isomer, said method comprising the steps of:

(a) reacting a compound of the formula

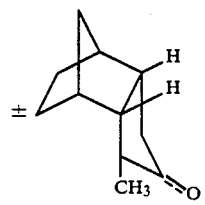

with the compound (2S,3S)-2,3-butanediol;

(b) hydrolyzing the product of (a);
(c) oxidizing the product of (b) by peracid oxidation using a peracid as oxidizing agent;
(d) reducing the product of (c);
(e) oxidizing the product of (d) and isometizing the resultant product with base to provide a methyl ketone;
(f) reacting the methyl ketone product of (e) with 4-phenyl-3-thiosemicarbazide; and where appropriate
(g) forming a pharmaceutically acceptable salt of the product of (f).

4. A method according to claim 3, wherein the final compound has a carbon-carbon double bond of the cis (Z) configuration in the group —CH$_2$—CH=CH—CH$_2$—CH$_2$—CH$_2$—COOH or its pharmaceutically acceptable salt.

* * * * *

UNITED STATES PATENT AND TRADEMARK OFFICE
CERTIFICATE OF CORRECTION

PATENT NO. : 4,992,581

DATED : February 12, 1991

INVENTOR(S) : GARLAND et al

It is certified that error appears in the above-identified patent and that said Letters Patent is hereby corrected as shown below:

Claim 2 line 3 delete "(2S,3S)-2-butanediol" and replace by --(2S,3S)-2,3-butanediol--.

Signed and Sealed this

First Day of October, 1991

Attest:

HARRY F. MANBECK, JR.

*Attesting Officer*  Commissioner of Patents and Trademarks